United States Patent [19]

Knowles et al.

[11] Patent Number: 4,645,738

[45] Date of Patent: Feb. 24, 1987

[54] METHOD FOR DIFFERENTIAL DIAGNOSIS OF T CELL LEUKEMIAS USING MONOCLONAL ANTIBODIES

[75] Inventors: Robert W. Knowles, New York; Bo Dupont, Harrison; Kazuyuki Naito, New York, all of N.Y.; Yasuo Morishima, Nagoya, Japan

[73] Assignee: Memorial Sloan-Kettering Institute Cancer Center, New York, N.Y.

[21] Appl. No.: 537,977

[22] Filed: Sep. 30, 1983

[51] Int. Cl.$^4$ .................. G01N 33/53; G01N 33/554; G01N 33/577

[52] U.S. Cl. .......................... 435/7; 436/519; 436/520; 436/536; 436/537; 436/548; 436/811; 436/813; 436/503; 935/104; 935/106; 935/108; 935/110

[58] Field of Search ............... 436/536, 537, 519, 520, 436/548, 503; 435/7; 935/104, 106, 108, 110

[56] References Cited

U.S. PATENT DOCUMENTS

| | | | |
|---|---|---|---|
| 4,361,549 | 11/1982 | Kung et al. | 935/106 |
| 4,361,550 | 11/1982 | Kung et al. | 935/106 |
| 4,363,799 | 12/1982 | Kung et al. | 935/106 |
| 4,364,937 | 12/1982 | Kung et al. | 935/104 |
| 4,381,295 | 4/1983 | Kung et al. | 935/104 |

FOREIGN PATENT DOCUMENTS 97518  1/1984  European Pat. Off. ............ 935/110

OTHER PUBLICATIONS

Bai et al., Evr. J. Immunol., 131 (1983) 521–7.
Deng et al., The Lancet, 1/2/82, 10–11.
Reinherz et al., J. Immunol. 123 (1979) 1312–7.
Reinherz et al., Proc. Natl. Acad. Sci. USA, 77 (1980) 1588–92.
Knowles, II et al., Blood, 62 (1983) 191–9.
Haynes et al., Proc. Natl. Acad. Sci. USA, 76 (1989) 1529–33.
Naito et al., Blood, 62 (1983) 852–5.

*Primary Examiner*—Christine M. Nucker
*Attorney, Agent, or Firm*—Felfe & Lynch

[57] ABSTRACT

Two monoclonal antibodies (3-3 and 3-40) were produced which identify two new leukemia associated antigens. Both antibodies reacted with most cell lines derived from patients with T lymphoblastic leukemia (T-ALL), but were not detected on suspensions of normal hematopoietic cells, including thymocytes, by cytotoxicity, absorption of indirect immunofluorescence assays. Analysis of fresh leukemic cells indicated that mAb 3-3 only reacted with T-ALL cells, while mAb 3-40 reacted with some non-T non-B ALL cells and a few acute myelocytic leukemia (AML) cells, as well as T-ALL cells. The 3-40 antigen was also found histopathologically in frozen sections of several normal tissues, including the epithelial cells and a few lymphoid cells of the thymus, and some malignant tissues, while the 3-3 antigen was not found in any tissue studied. A "double absorption" assay provided additional serological evidence the the two antibodies identify different antigenic determinants. Biochemical analysis indicated that the molecules immunoprecipitated by mAb 3-3 and mAb 3-40 have molecular weights of 35–40,000 daltons. It is demonstrated that the 3-3 and 3-40 antigens are markers for human T-ALL and can be used along with the normal T lymphocyte antigen, 3A1, to discriminate T-ALL from cutaneous T-cell lymphoma (CTCL), adult T cell leukemia (ATL) and T cell chronic lymphocytic leukemia (T-CLL).

7 Claims, No Drawings

METHOD FOR DIFFERENTIAL DIAGNOSIS OF T CELL LEUKEMIAS USING MONOCLONAL ANTIBODIES

This invention was partially made with grants from the U.S. Public Health Services, NIH-NCI CA-22507, Ca-08748 and CA-23766. Therefore, the U.S. Government has certain rights in this invention.

The present invention relates to monoclonal antibodies against T cell leukemias. These antibodies are useful in differential diagnosis in leukemia. A use in diabetes is also discovered.

BACKGROUND

Conventional antisera, produced by immunizing animals with tumor cells or other antigens, contain a myriad of different antibodies differing in their specificity and properties. In 1975 Köhler and Milstein (Nature, 256:495) introduced a procedure which leads to the production of quantities of antibodies of precise and reproducible specificity. The Köhler-Milstein procedure involves the fusion of spleen cells (from an immunized animal) with an immortal myeloma cell line. By antibody testing of the fused cells (hybridomas), clones of the hybridomas are selected that produce antibody of the desired specificity. Each clone continues to produce only that one antibody, monoclonal antibody (mAb). As hybridoma cells can be cultured indefinitely (or stored frozen in liquid nitrogen), a constant supply of antibody with uniform characteristics is assured.

Antibodies are proteins that have the ability to combined with and recognize other molecous, known as antigens. Monoclonal antibodies are no different from other antibodies except that they are very uniform in their properties and recognize only one antigen or a portion of an antigen known as a determinant.

In the case of cells, the determinant recognized is an antigen on or in the cell which reacts with the antibody. It is through these cell antigens that a particular antibody recognizes, i.e. reacts with, a particular kind of cell. Thus the cell antigens are *markers* by which the cell is identified.

These antigenic markers may be used to observe the normal process of cell differentiation and to locate abnormalities within a given cell system. The process of differentiation is accompanied by changes in the cell surface antigenic phenotype, and antigens that distinguish cells belonging to distinct differentiation lineages or distinguish cells at different phases in the same differentiation lineage may be observed if the correct antibody is available.

The preparation of hybridoma cell lines can be successful or not depending on such experimental factors as nature of the innoculant, cell growth conditions, hybridization conditions etc. Thus it is not always possible to predict successful hybridoma preparation of one cell line although success may have been achieved with another cell line.

Progress in defining cell surface antigens is of great importance in differentiation and disease as markers for normal and diseased cells furthering diagnosis and treatment. Thus work on melanocytes was made possible by the recently discovered technique of culturing melanocytes from normal skin (Eisinger, et al., Proc. Nat'l. Acad. Sci. USA, 79 2018 (March 1982). This method provides a renewable source of proliferating cells for the analysis of melanocyte differentiation antigens. Likewise, a large number of cell lines derived from melanomas have now been established and these have facilitated the analysis of melanoma surface antigens. The advent of mAbs has greatly accelerated knowledge about the surface antigens of malignant melanoma. Cells markers on both melanomas and melanocytes have been identified. A panel of typing monoclonal antibodies has been selected which recognizes differentiation antigen characteristics at each stage of development in both melanocytes and melanomas. These differentiation antigens may be used to classify melanocytes and melanomas and to group them into characteristic sub-sets. Dippold et al. *Proc. Nat'l. Acad. Sci. U.S.A.* 77, 6114 (1980) and Houghton, et al. *J. Exp. Med.* 156, 1755 (1982). Immunoassay of melanocytes and melanoma cells within sub-sets is thus made possible.

Initial recognition of differentiation antigens came about through analysis of surface antigens of T-cell leukemias of the mouse and the description of the TL, Thy-1, and Lyt series of antigens. (Old, Lloyd J., Cancer Research, 41, 361–375, February 1981) The analysis of these T-cell differentiation antigens was greatly simplified by the availability of normal T cells and B cells of mouse and man. (See U.S. Pat. Nos. 4,361,549–559; 4,364,932–37 and 4,363,799 concerning mAb to Human T-cell antigens).

The existence of human leukemia specific antigens has been suggested by studies using heterologous antibodies developed by immunization with human leukemic cells [Greaves, M. F. et al. Clin. Immunol. and Immunopathol 4:67, (1975); Minowada, J., et al. J. Nat'l. Cancer Insti. 60:1269, (1978); Tanigaki, N., et al. J. Immunol. 123:2906, (1979)] or by using autologous antisera obtained from patients with leukemia [Garret, T. J., et al., Proc. Nat'l. Acad. Sci. USA 74:4587, (1977); Natio, K., et al., Proc. Nat'l. Acad. Sci. USA, 80: 2341, (1983)]. The common acute lymphoblastic leukemia antigen (CALLA) which is present on leukemia cells from many patents with non-T, non-B, acute lymphoblastic leukemia (N-ALL), some chronic myelocytic leukemias (CML) in blast crisis and a few acute T-lymphoblastic leukemias (T-ALL) was originally described using conventional rabbit heteroantisera [Greaves, M. F. et al. Supra). By the autologous typing technique (Garret, T. J., et al. Supra; Naito, K., et al. Supra 1983; Old, L. J. Cancer Res. 41:36, (1981)], antibodies uniquely reacting with ALL cells were found in sera obtained from patients with ALL, and seemed to recognize very similar antigens to CALLA (Garret, T. J., et al. Supra; Naito, K., et al. Supra). Another leukemia associated antigen detected by heterologous antisera is the human thymus leukemia (TL)-like antigen, which is present on thymocytes as well as leukemia cells (Tanigaki, N. et al. Supra). This antigen, is therefore, a normal differentiation antigen which is composed of a heavy chain (MW 44,00–49,000) and light chain (MW 12,000–14,000) similar to the class I HLA antigens (Tanigaki, N., et al. Supra). These investigations have, however, been hampered by the need for vigorous absorptions with normal tissues as well as the relatively small quantity and low titer of the antisera.

In vitro production of monoclonal antibodies by the technique of Köhler and Milstein, Supra has provided a better system for the identification and detection of leukemia specific antigens. A panel of monoclonal antibodies detecting cell surface antigens of human peripheral blood lymphocytes and their precursor cells have been investigated in detail [Reinherz, E. L., et al. Proc.

Nat'l. Acad. Sci. USA 77:1588, (1980)]. While monoclonal antibodies detecting antigens characteristic for different lymphocyte lineages can be used for classification of human lymphocytic leukemia [Schroff, R. W., et al. Blood 59: 207, (1982)], such antibodies have only limited therapeutic applications. Monoclonal antibodies detecting human leukemia associated antigens have also been produced. These include several antibodies detecting the human equivalents of the murine TL antigens. One TL-like antigen is recognized by NA1/34 [McMicheal, A. J., et al. Eur. J. Immunol. 9:205, (1979)], OKT6 (Reinherz, E. L., et al. Supra) and Leu 6 (R. Evans, personal communication). A second TL-like antigen is recognized by M241 (Knowles, R. W., et al. Eur. J. Immunol. 12: 676,1982). Monoclonal antobodies with specificities for common acute lymphoblastic leukemia antigens J-5 (Ritz, J., et al. Nature 283:583, 1980), NL-1 and NL-22 (Ueda, R., et al. Proc. Nat'l. Acad. Sci. USA 79:4386, 1982) have also been produced. Recently, Deng, C-T, et al. Lancet. i:10, 1982) reported a complement fixing monoclonal antibody (CALLA-2) which reacts with most cultured human T-ALL cell lines and also reacts with most fresh T-ALL cells.

SUMMARY

The present invention describes two new monoclonal antibodies associated with leukemia. These mAbs (3-3 and 3-40) detect two distinct human leukemia associated antigens. These leukemia associated antigens were found to be expressed in the vast majority of T-cell acute lymphoblastic leukemias. This work is described in a forthcoming issue of *Blood* of October 1983 which is hereby incorporated by reference. Both antibodies reacted with cell lines derived from patients with T lymphoblastic leukemia (T-ALL), but were not detected on suspensions of normal hematopoietic cells, including thymocytes, by cytotoxicity, absorption or indirect immunofluorescence assays. Analysis of fresh leukemia cells indicated that mAb 3-3 only reacted with T-All cells, while mAb 3-40 in addition reacted with some non-T non-B ALL cells and a few acute myelocytic leukemia (AML) cells. The mAb 3-40 defined antigen (3-40 antigen) was also found histopathologically in frozen sections of several normal tissues, including the epithelial cells and a few lymphoid cells of the thymus, and some malignant tissues. The mAb 3-3 defined antigen (3-3 antigen) was not found in any tissue studied. A "double absorption" assay provided additional serological evidence that the two antibodies identify different antigenic determinants. Biochemical analysis indicated that the molecules immunoprecipitated by mAb 3-3 and mAb 3-40 have molecular weights of 35–40,000 daltons. It is demonstrated that the 3-3 and 3-40 antigens are markers for human T-ALL and can be used to discriminate T-ALL from cutaneous T-cell lymphoma (CTCL), adult T cell leukemia (ATL) and T cell chronic lymphocytic leukemia (T-CLL).

DESCRIPTION

Production of mAb

Two antibody producing hybridomas (CL 3-3 and CL 3-40) were developed using the technique of Köhler and Milstein, Supra. Briefly, BALB/c mice were immunized three times with the T-ALL cell line MOLT-4 ($1 \times 10^7$ cells) every two weeks. Three days after the last immunization, splenocytes form the immunized mice were fused with mouse myeloma cell line NS-1 using a 40% solution of polyethylene glycol 4000 (Sigma, St. Louis, MO). Fused cells were selectively grown by culturing in RPMI 1640 supplemented with 15% fetal calf serum (FCS), hypoxanthine, aminopterin and thymidine in flat bottom microculture plates (Cat #3596, Costar, Cambridge, MA). For the initial screening, the supernatant of each culture well was tested by complement-dependent cytotoxicity testing on the immunizing cell line MOLT-4 and peripheral blood T lymphocytes. The two hybridoma cultures with selective reactivity against MOLT-4 were subsequently established as clones (cl) by two successive limiting dilutions. Both antibodies were developed as ascites fluid by intraperitoneal injection of the cloned hybridoma cells into BALB/c mice. A titer of more than 1:100,000 was obtained for both complement fixing antibodies. Another hybridoma clone designated as CL 1-3, detecting the 3Al antigen (Haynes, B. F., et al. Proc. Nat'l. Acad. Sci. USA 76: 5829, 1979; Haynes, B. F., et al. N. Engl. J. Med. 304:13 9, 1981), was established by fusion between NS-1 and splenocytes form a mouse immunized with human Concavalin A (Con A) stimulated splenocytes. The mAb 1-3 was demonstrated to detect the same antigen as 3Al by sequential immunoprecipitations with the antibodies 3Al, 4A (Morishima, Y. et al. J. Immunol. 129: 109, 1982), and mAb 1-3. The serological analysis using mAb 1-3 confirmed previous reports (Haynes, B. F., et al. Supra, 1979; Haynes, B. F., et al. Supra, 1981, Morishima et al. Supra) that the distribution of this antigen is restricted to T-lymphocytes and T-ALL cells (data not shown). Monoclonal antibodies NL-1, which detects a similar antigen to common ALL antigen CALLA), was kindly provided by Dr. R. Ueda, Aichi Cancer Center, Japan (Ueda, R., et al. Supra). Monoclonal antibody 6A (Morishima, Y. et al. Supra) which detects a common determinant of human HLA-DR antigens, and mAb 4E, which detects a common determinant of the human HLA-B antigen (Yang, et al., unpublished observations), were produced in this laboratory. Two mAbs NA1/34 (McMichael, A. J., et al. Supra) and M241 (Knowles, R. W., et al. Supra, 1982) which recognize human TL-like molecules, the mAb W6/32 (Barnstable, C. J., et al. Cell 14: 9, 1978) recognizing a common determinant of human HLA-A,B,C antigens and BBM.1 (Brodsky, F. M., et al. Eur. J. Immunol. 9:536, 1979) recognizing human B$_2$ (Beta sub-two) microglobulin were included in the biochemical analysis.

Cell Preparation

Heparinized peripheral blood was collected from healthy adult donors and the peripheral blood mononuclear leukocytes (PBL) were isolated by Ficoll-Hypaque density gradient centrifugation (Lymphoprep, Accurate Chemical Co., Hicksville, NY) (Böyum, A. J. Clin. Lab. Invest. 97:21s, 1968). T- and B- lymphocytes were prepared by passing PBL suspension over a nylon-wool column (Leuko-pak leukocyte filter, Fenwal Labs, Travenol, IL) as described by Danilovs et al (Danlilovs, J. A., et al. In: Histocompatability Testing 1980, UCLA Tissue Typing Laboratory, California, ed. P. I. Terasaki, P. 287). Briefly, 45 min. after incubation of $15-20 \times 10^6$ PBL cells in the nylon wool column, the T-cell enriched fraction was eluted with 10 ml of RPMI 1640 with 10% fetal calf serum (FCS). The B cell enriched cell fraction was collected by squeezing the column with a plunger. The T cell enriched population contained more than 95% sheep red blood cells rosette (E-rosette) forming cells while the B cell enriched population consisted of more than 80% surface immunoglobulin positive cells which were determined by direct immunofluorescence using fluorescein (FITC) conjugated F(ab')$_2$ fragment of goat anti-human Ig (Cappel Labs., Cochranville PA).

Adherent mononuclear cells (monocytes) were obtained by incubating PBL ($1 \times 10^7$ in 5 ml of RPMI 1640 with 10% FCS) in $60 \times 15$ mm tissue culture dishes (Falcon plates, Oxnard, CA) for 60 min at 37° C. After the non-adherent cells were removed by washing in RPMI 1640, the monocytes were detached by further incubation in phosphate buffered saline (PBS) containing 0.2% ethylenediametetracetic acid (EDTA) and 1% FCS. More than 80% cells in this preparation had the morphologic characteristics of monocytes. 6% dextran sulfate in saline (Abbot Labs, Chicago, IL) was employed to collect polymorphonuclear leukocytes (granulocytes) and red blood cells. After mixing this solution with the heparinized blood, granulocytes were recovered from the supernatant and red blood cells were recovered from the sediment. More than 95% of cells in the granulocyte preparations had the morphologic characteristics of granulocytes.

In Vitro Transformed Lymphocytes

In vitro transformed lymphocytes were tested for reactivity with the antibodies at the peak of blast transformation (i.e., phytohaemagglutinin (PHA): day 3, Con A: day 4, MLC: day 5). The lymphocytes were stimulation with either PHA-16 (Difco, Detroit, MI) at 1.25 microgram/ml or Con A (Pharmarcia, Sweden and Piscataway, NJ) at 20 microgram/ml. PHA- and Con A- stimulated lymphocytes were incubated in RPMI 1640 supplemented with 10% human serum (HS) supplemented with 2 mM-glutamine, penicillin 100 U/ml, and streptomycin 100 microgram/ml at 37° C. in a humidified atmosphere containing 5% $CO_2$. The one-way mixed lymphocyte cultures (MLC) were performed between peripheral blood lymphocytes (PBL) from unrelated HLA-D incompatible donors. The stimulator cells were irradiated with 2000 rads.

In addition, several T cell clones, which were established after mixed lymphocyte culture (MLC) using interleukin-2 (Biotest, W. Germany) and cloned on soft agar (Flomenberg, N., et al. Immunogenetics (in press), 1983) were employed in the serological study.

Other Hematopoietic Tissues

Bone marrow mononuclear cells were isolated by Ficoll-Hypaque density gradient centrifugation. Thymocytes were obtained from the thymuses of childern who had undergone cardiac surgery. Spleen cells were prepared from spleens obtained during abdominal surgery. Thymuses, spleens and bone marrow were histologically documented as normal. The tissues were prepared by mincing and filtering the resulting cell suspension through a metal mesh.

Fresh Leukemia and Lymphoma Cells

Fresh leukemia cells were isolated from heparinized peripheral blood and/or bone marrow using Ficoll-Hypaque density gradient centrifugation (Böyum, A., Supra). More than 90% of the cells in the samples were morphologically leukemic cells.

Lymphoma cells were prepared into single cell suspensions as described for samples of thymus and spleen.

In some cases, leukemic and lymphoma cells were cryopreserved and stored in the liquid nitrogen until studied.

Most of the leukemic cells used in this study, particularly the cells reported in Table III, were provided by Professor K. Yamada, Nagoya Medical University, Japan. The Sezary cells were provided by Dr. B. Safai, Dermatology Service, Memorial Hospital. The diagnostic criteria for the different types of leukemia and lymphoma are determined by the usual hematologic and clinical principals. In brief, E-rosette positivity denotes that more than 20% of the cells were able to form a sheep red blood cell (SRBC) rosettes (Weiner, M. S., et al. Blood 42:939, 1973), which is regarded as a criterion for the T cell lineage of leukemia cells. EAC rosette positivity denotes that more than 20% of the cells formed rosettes with SRBC sensitized with rabbit antisera (IgM) coated with mouse complement (Ross, G. D., et al. In: In vitro Methods in cell mediated and Tumor Immunology, eds. B. R. Bloom and J. R. David, Academic Press, New York, p. 123, 1976) and is employed as the criterion of B cell lineage of the leukemia cells. The ALL cases, in which less than 20% of the cells were able to form the E-rosette, but had other T-ALL associated phenotypes (i.e., HLA-DR negative and 3Al antigen positive) and/or the existence of thymoma, were included in the T-ALL group. Other All cases were classified as the non-T, non-B ALL (N-ALL) group. Adult T cell leukemia (ATL) was diagnosed according to the criteria proposed originally by Uchiyama et al. (Uchiyama, T. et al. Blood, 50:481, 1977). The diagnosis of Sezary syndrome was based on the clinical criteria reported by Lutzner et al. (Lutzner, M. et al. Ann. Intern. Med. 83:534–552, 1975). For the diagnosis of myeloid malignancy, cytochemical studies were performed, including peroxidase, napthol-ASD-chloracetate esterase (N-ASD-C) (Yam, L. T., et al. Amer. J. Clin. Pathol. 55: 283, 1971), and alpha-napthylbutyrate esterase (a-N-B) (Li, C. Y., et al. J. HIstochem. Cytochem. 21: 1, 1973). Double staining for both esterases was also done in some cases.

In Vitro Cultured Cell Lines

The hematopoietic cell lines were obtained locally or from other investigators. The T lymphblastoid cell lines (T cell lines) used were: HSB-2 and CCRF-CEM from the American Type Culture Collection (ATCC), MOLT 4, and RPMI 8402 from Dr. J. Minowada, Rosswell Park Memorial Institute, MOLT-3 and Hogan from Dr. Ohnuma, Mt. Sinai Medical Center, NY, 45 and JURKAT from Dr. P. Ralph, Sloan-Kettering Institute for Cancer Research (SKI), and HUT 78 and HUT 102 developed by Dr. R. Gallo, NCI, and obtained from Dr. L. Old, SKI. The following B lymphoid cell lines (B cell lines) were used: DAUDI from Dr. G. Klein, Stockholm, WALK-1, REMB, FS-2, FB1B, AUR, WT-52 from SKI, SB from ATCC, RPMI-8422 and DND-39A from Dr. Ohnuma and SK-LY-16, SK-LY-18 and BALL-1 from Dr. L. Old. The erythroid cell line K562 was provided by Dr. G. Klein, Stockholm. Two B-cell lines, ARH-77 and ARA-10, two myeloid cell lines, KG-1 and HL-60, and the monocytic cell line U-937 were obtained from Dr. P. Ralph, SKI, and two non-T, non-B cell lines NALL-1 and NALM-1 from Dr. L. Old, SKI. All hematopoietic cell lines were maintained in culture medium containing RPMI 1640 supplemented with 10% FCS, 100 U penicillin, 100 micrograms streptomycin and 2 mM L-glutamine per ml and cultured at 37° C. in humidified 5% $CO_2$ incubator.

Tumor cell lines established in vitro from non-hematopoietic tissues were obtained from the cell library of Dr. L. Old. SKI. The cell lines used were: bladder tumor T-24 and J-82, melanoma SK-MEL-19 and SK-MEL-37, brain tumor AJ, renal tumor SK-RC-7, lung tumor SK-LC-LL, uterine tumor ME-180, liver tumor SK-HEP, 1, colon tumor SW-1222 osteosarcoma U-20S. All non-hematopoietic tumor cell lines were maintained in Eagle Minimum Essential Medium supplemented with 10% FCS, 2 mM L-glutamine, penicillin and streptomycin.

HLA typing of the cell lines was used to exclude cross-contamination of cell lines as described by Hansen et al. (Hansen, J. A., et al. Immunogenetics 8: 51, 1979) and Pollack et al. (Pollack, M. S., et al. Tissue Antigens 15:249, 1980).

Indirect Immunofluorescence

The indirect immunofluorescence was performed with saturating concentrations of mAb 3-3 and mAb 3-40 culture supernatants or ascites. $1 \times 10^6$ cells were incubated with 0.05 ml of mAb3-3 or mAb 3-40 at 4° C. for 30 min. Excess antibody was removed by washing with PBS containing 0.4% bovine serum albumin and 0.02% sodium azide ($PBS-NaN_3$). Then 0.05 ml FITC conjugated goat-anti-mouse immunoglobulin (1:10 dilution) (DAKO, Westbuty, NY) was added and incubated for another 30 min at 4° C. These cells were further washed in $PBS-NaN_3$, and the percentage of fluorescence positive cells was counted for more than 200 cells in the samples using a phase contrast fluorescent microscope (Leitz, W. Germany). Selected samples were also analyzed using a fluorescence activated cell sorter (FACS IV) (Becton-Dickinson, Mountain View, CA).

Complement-dependent Microcytotoxicity Test (C'-Cytotoxicity Test)

The standard two stage NIH complement dependent microcytotoxicity technique was employed (Mittal, K. K., Transplantation 25: 275, 1978). 60 well microtest plates (Cat #3034, Becton-Dickinson, Cockysville, MD) were prepared with 1 microliter of saturating concentrations of mAb 3-3 or 3-40 sealed under paraffin oil. 1 microliter of cell suspension ($3 \times 10^6$ cells/ml) was added to each well with a microdispenser. After incubation at 22° C. for 30 min, 5 microliter of prescreened rabbit serum was added as a complement source. After an additional incubation at 22° C. for 45 min, eosin was added and the plates were read with an inverted microscope.

Absorption Assay

Absorption was performed using $10^7$ cells growing in suspension culture or 50 microliter packed cells for tumor cells or erythrocytes. The cells were incubated at 4° C. for 1 hour with 0.05 ml of antibody. Antibody for absorption was used at a concentration determined by previous studies at four-fold higher concentration than the amount required for 50% killing of the target cell, MOLT-4. The remaining reactivity of antibody was then determined with C'-cytoxicity test and the percentage of living and dead cells were determined.

"Double Absorption" Assay for Detection of Serological Cross-Reactivity

In this "double absorption" assay, aliquots of $10^7$ MOLT 4 cells were incubated with saturating amounts of either mAb 3-3 or mAb 3-40 for 1 hour at 4° C. Cells coated with mAb 3-3, cells coated with mAb 3-40 or uncoated cells were then tested in parallel for their ability to absorb either mAb 3-3 or mAb 3-40 at the appropriate concentration using the absorption assay described above. If both antibodies recognize the same epitope or a determinant located in close proximity on the cell surface, then the cells coated with one antibody would no longer be capable of absorbing the reactivity of the other antibody.

Immunofluorescence on Frozen Sections

Indirect immunofluorescence was performed using frozen sections of normal and malignant tissues. All fresh tissues were snap frozen in liquid nitrogen and stored at −70° C. Three to five micron sections of tissues were cut with a Bright cryostat and stored at −70° C. if not used immediately. Tissue sections were fixed in 3.7% formaldehyde for 10 minutes at room temperature. The sections were washed three times with phosphate buffered saline (PBS) and incubated for one hour in a humid chamber with hybridoma supernatant or ascites. The slides were washed three times with PBS and incubated for 30–60 minutes with the appropriate dilution of a FITC-labeled IgG fraction of goat anti-mouse immunoglobulin (Cappel laboratory). After washing three times with PBS, the sections were mounted with buffered glycerol and read under a Leitz Dialux 20 fluorescence microscope with epi-illumination. For some specimens, immunoperoxidase staining was employed, in addition to indirect immunofluorescence.

Determination of Immunoglobulin (Ig) Subclass of mAbs 3-3, 3-40, and 1-3

Cultured supernatants of mAb 3-3, 3-40 and 1-3 were concentrated 5 times and their Ig subclasses were determined by the double immunodiffusion method, using goat or rabbit antisera to mouse IgM, $IgG_1$, $IgG_{2a}$, $IgG_{2b}$, and $IgG_3$ (Litton Bionetic, Kensington, MD). Consequently, mAb 3-3 was $IgG_{2b}$ K, mAb 3-40 was IgM K and mAb 1-3 was $IgG_{2a}$ K.

Biochemical Analysis of the 3-3 and 3-40 Antigens

The molecular weights of the 3-3 and 3-40 antigens were examined following immunoprecipitation from lysates of $^{125}I$ surface labeled MOLT 4 cells. Intact MOLT 4 cells were labeled with $^{125}I$ using lactoperoxidase and lysed with 0.5% NP-40, as described previously (Knowles, R. W., et al. Supra, 1982). Solubilized antigens were immunoprecipitated using ascites fluid containing mAb 3-3 or mAb 3-40 in parallel with NA1/34 (McMichael, A. J., et al. Supra) and M241 (Knowles, R. W., et al. Supra 1982), which recognize two distinct human thymus leukemia-like antigens. Also included were W6/32 (Barnstable, C. J., et al., Supra) which recognizes the heavy chain of HLA-A,B,C molecules and BBM.1 (Brodsky, F. M., et al., Supra) which recognizes B2(Beta-subtwo)-microglobulin. SDS polyacrylamide gel electrophoresis was performed as described by Laemmli (Laemmli, U. K., Nature 227: 680, 1970) using either 12.5% or 15% slab gels. Gels were fixed in trichloroacetic acid, stained with Coomassie Brilliant Blue, destained and dried for autoradiography which was performed using Kodak XAR-5 film with Cronex fluorescent screens (DuPont) at −70° C. The following examples of results are for illustrative purposes only and are not meant to limit the invention.

EXAMPLE 1

Tissue Distribution of 3-3 and 3-40 antigens

The tissue distribution of the antigens detected by the two monoclonal antibodies mAb 3-3 and mAb 3-40 is presented in Table 1 and 2 below. There was very good agreement between the results obtained with the C'-cytotoxicity test and with the absorption test. These human hematopoietic cell lines were also tested by indirect immunofluorescence microscopy. For the few cell lines where the C'-cytotoxicity test was negative, but the absorption test was positive, the If test was also positive. For example, the T cell line CCRF-CEM was completely negative for mAb 3-3 with C'-cytotoxicity test, while 15% of the cells were positive with the indirect immunofluorescence test and CEM cells removed the antibody in absorption tests. Monoclonal antibody 3-3 reacts with all T-ALL cell lines except HSB-2. Monoclonal antibody 3-40 reacts with all T-ALL cell lines except HOGAN. To exclude the possibility that these antigens were induced by growth in heterologous serum, two T-ALL cell lines, MOLT-4 and 45, were cultured for more than one month in RPMI 1640 supplemental with 10% human serum instead of fetal calf serum. Both cell lines continued to express the 3-3 and 3-40 antigens after being cultured with human serum, when assayed by either C'-cytotoxicity or absorption tests. T cell lymphoma/leukemia cell lines, HUT-102 (HTLV producer) and HUT-78 (HTLV non-producer) (Poiesz, B. J. et al. Proc. Nat'l. Acad. Sci. USA 77: 7415, 1980) do not express the antigens detected by mAb 3-3 and mAb 3-40. All B cell lines, myeloma cell lines, non-T, non-B lymphoid cells and myeloid cell lines failed to react with either mAb 3-3 or mAb 3-40. Non-hematopoietic cell lines were only tested by absorption, and all of the cell lines were negative for these antigens. Four non-human cell lines of hemopoietic origin, including two murine T leukemia cell lines EL-4, RLo1, were also negative for these antigens.

TABLE I

Distribution of 3-3 and 3-40 Antigen

| Cell Lines | Cell ID | mAb 3-3 Ab + C'[1] | mAb 3-3 Absorption[2] | mAb 3-40 Ab + C'[1] | mAb 3-40 Absorption |
|---|---|---|---|---|---|
| T—ALL | MOLT-4 | + | + | + | + |
|  | MOLT-3 | + | + | + | + |
|  | 45 | + | + | + | + |
|  | RPMI-8402 | + | + | + | + |
|  | JURKAT | + | + | + | + |
|  | CCRF-CEM | − | + | + | + |
|  | HSB-2 | − | − | + | + |
|  | HOGAN | + | ND | − | ND |
| T—CTL | HUT-102* | − | ND | − | ND |
|  | HUT-78** | − | ND | − | ND |
| B—LCL (EBV) | WALK-1;REMB;SB-2; FS-2;FB1B;WT-52; AUR;RPMI-8422 | − | − | − | − |
| B—LCL | ARH-77***;ARA-10*** | − | − | − | − |
| B—LCL (Burkitt) | DAUDI;RAJI;DND-39A | − | − | − | − |
| B Lymphoma | SK-LY-16;SK-LY-18 | − | − | − | − |
| B—ALL | BALL-1 | − | − | − | − |
| Non-T,Non-B ALL | NALL-1;NALM-1 | − | − | − | − |
| Myeloid | K562;U937;KG1;HL-60 | − | − | − | − |
| Non-hematoboietic tumors |  |  |  |  |  |
| Bladder | T-24;J-82 | NA | − | NA | − |
| Melanoma | SK-MEL-19;SK-MEL | NA | − | NA | − |
| Brain | AJ | NA | − | NA | − |
| Kidney | SK-RC-7 | NA | − | NA | − |
| Lung | SK-LC-LL | NA | − | NA | − |
| Uterus | ME 180 | NA | − | NA | − |
| Liver | SK-HEP-1 | NA | − | NA | − |
| Colon | SW-1222 | NA | − | NA | − |
| Bone | U-20S | NA | − | NA | − |
| Non-Human Lines |  |  |  |  |  |
| B—LCL (EBV) (Monkey) | HR-1 | ND | − | ND | − |
| Myeloma (Mouse) | P3-NS-1/1-Ag 4 | ND | − | ND | − |
| T—Leukemia (Mouse) | EL-4;RLo1 | − | ND | − | ND |

Legend to Table I:
For all cells, + indicates positive for the antigen and − indicates negative for the antigen. NA denotes not applicable; ND denotes not done.
T—ALL, denotes T acute lymphoblastic leukemia; T—CTL, denotes cutaneous T—cell leukemia/lymphoma; B—LCL, denotes B—lymphoblastic cell lines; EBV, denotes B—LCL established by EB virus transformation; Burkitt, denotes B—LCL established from patients with Burkitt's lymphoma; B—ALL, denotes acute B—lymphoblastic leukemia; HUT-102*, human T leukemia virus (HTLV) producer; HUT-78, non-producer of HTLV. ARH-77* and ARA-10***, B—LCL established from patients with myeloma.
Complement dependent microcytotoxicity tests (1) and absorption tests (2) were performed as described above. In the cytotoxicity test, less than 10% killing was regarded as a negative case. More than 90% killing was obtained in all positive cases. Inthe indirect immunofluorescence test which was performed concomitantly, the same negative test samples demonstrated less than 5% staining. More than 50% staining evaluated by direct microscopy was obtained in all positive cases.
End Legend Table I

TABLE II

Summary of Tissue Distribution of 3-3 and 3-40 Antigens

| CELL TYPE | mAb 3-3 Ab + C' | mAb 3-3 Abs | mAb 3-40 Ab + C' | mAb 3-40 Abs |
|---|---|---|---|---|
| A. Normal Cells |  |  |  |  |
| T-lymphocytes | 0/20 | 0/4 | 0/20 | 0/4 |
| B-lymphocytes | 0/20 | 0/2 | 0/20 | 0/2 |

TABLE II-continued

Summary of Tissue Distribution of 3-3 and 3-40 Antigens

| CELL TYPE | mAb 3-3 Ab + C' | mAb 3-3 Abs | mAb 3-40 Ab + C' | mAb 3-40 Abs |
|---|---|---|---|---|
| Thymocytes[1] | 0/4 | 0/3 | 0/4 | 0/3 |
| Splenocytes | 0/3 | 0/3 | 0/3 | 0/3 |
| PHA-blasts | 0/2 | 0/1 | 0/2 | 0/1 |
| Con A-blasts | 0/2 | 0/1 | 0/2 | 0/1 |
| MLC-blasts | 0/1 | 0/1 | 0/1 | 0/1 |
| T cell clones | 0/22 | ND | 0/22 | ND |
| Granulocytes | 0/3 | ND | 0/3 | ND |
| Monocytes | 0/3 | ND | 0/3 | ND |
| Bone Marrow | 0/5 | ND | 0/5 | ND |
| Erythorcytes | NA | 0/2 | NA | 0/2 |
| Fibroblasts | 0/ | ND | 0/ | ND |
| B. Leukemia and Lymphoma Cells[2] | | | | |
| T-ALL | 9/11 | 8/9 | 8/11 | 8/9 |
| B-ALL | 0/2 | 0/1 | 0/2 | 0/1 |
| Non-T, Non-B ALL | 0/9 | 0/4 | 5/9 | 3/5 |
| TL | 1/2 | 1/2 | 2/3 | 1/2 |
| Sezary | 0/3 | 0/2 | 0/3 | 0/2 |
| ATL | 0/3 | 0/3 | 0/3 | 0/3 |
| T-CLL | 0/1 | 0/1 | 0/1 | 0/1 |
| B-CLL | 0/25 | 0/2 | 0/25 | 0/2 |
| AML | 0/6 | 0/6 | 1/5 | 2/4 |
| AMOL | 0/3 | 0/3 | 0/3 | 0/3 |
| CML (Blast Crisis) | 0/1 | 0/1 | 0/1 | 0/1 |

Legend to Table II:
The ratio in this table indicates the number of positive cases to the number of total cases. NA denotes not applicable; ND denotes not done.
(1) One of 4 thymocytes was derived from fetal material.
(2) The diagnostic criteria employed for leukemia and lymphoma are described above.
(3) In cytotoxicity testing, less than 10% killing was obtained in all cell types except thymocytes, granulocytes and monocytes. For these cell types, less than 20% killing was accepted as negative.
End Legend Table II The tissue distribution of the 3-3 and 3-40 antigens on cultured human cell lines suggested that both antigens are restricted to cell lines established from the patients with T-ALL. The serological analysis was therefore extended to a panel of fresh normal cells and leukemic cells. Normal peripheral blood cells (i.e., T-lymphocytes, B-lymphocytes, monocytes, granulocytes and erythrocytes) did not express either the 3-3 or the 3-40 antigen on their cell surfaces. In vitro transformed lymphocytes (i.e., PHA blasts, Con A blasts, and blast cells obtained from in vitro mixed lymphocyte culture [MLC] and interleukin-2 dependent, MLC stimulated, T cell clones) were also negative. Five fresh samples of thymocytes were negative for both antigens, including one sample of fetal thymocytes. Similarly, normal bone narrow cells, and splenocytes, did not express the antigens 3-3 and 3-40 (Table IIA). In summary, all normal hematopoietic cells tested in suspension by cytotoxicity, absorption and indirect immunofluorescence were negative for 3-3 and 3-40 antigens.

Purified peripheral blood T lymphocytes, fresh thymocytes, and cultured MOLT-4 cells were also studied using the fluoescence activated cell sorter (FACS IV). The normal T lymphocyte antigens, Leu 1, Leu 2a, and Leu 3a ) demonstrated the typical distributions as reported previously (Evans, R. L., et al. J. Exp. Med. 145: 221, 1977). The human TL-like antigen, recognized by anti-Leu 6 is expressed on both thymocytes and MOLT 4, although it was not found on the cell surface of T lymphocytes. Under parallel conditions, the 3-3 and 3-40 antigens were not detected on T lymphocytes or thymocytes, while MOLT-4 is brightly stained by both monoclonal antibodies.

The reactivities of mAb 3-3 and mAb 3-40 with bone marrow cells were also examined using the FACS IV. In this analysis, T lymphocytes as well as bone marrow cells were examined using 4E, a mAb reacting with HLA-B antigens and mAbs to the normal T lymphocyte antigens, Leu 1 and Leu 5, in parallel with mAb 3-3 and mAb 3-40. 4E, Leu 1 and Leu 5 reacted strongly with most T lymphocytes. Most bone marrow cells were positive with 4E, while only a small percentage were positive for Leu 1 and Leu 5. In contrast, positive cells were not detectable when bone marrow cells or T lymphocytes were examined using mAb 3-3 or mAb 3-40.

EXAMPLE 2

Expression of 3-3 and 3-40 antigen on fresh leukemia cells

In contrast to the studies on normal hematopoietic cells, it was found that mAb 3-3 and mAb 3-40 reacted with most T-ALL and T lymphoma cells. The data obtained by studying fresh leukemia cells are summarized in Table IIB above and in Table IIIA-C below. The mAb 3-3 only reacted with cells from patients with acute lymphoblastic leukemia of T-cell lineage. In contrast, it was found that mAb 3-40 also reacted with some non-T, non-B ALL and with two cases of AML. It should also be noted from Table IIB that none of the samples obtained from patients with Sezary syndrome, adult T-cell leukemia (ATL) or T-CLL, expressed the 3-3 or 3-40 antigen. A more detailed analysis of the cell surface phenotype of the leukemia cells is presented in Table IIIA-C below. The cells were tested with the mAbs 3-3 and 3-40, and with mAb NL-1 (Ueda, R., et al. Supra 1982) which detects the common ALL antigen (CALLA). The mAb NL-1 detects the same antigen as mAb J5 (Ritz, J., et al. Supra 1980), see above. Also included in the analysis is mAb 1-3, which detects the 3A1 antigen (Haynes, B. F., et al. Supra, 1979), and mAb 6A, detecting a common HLA-DR determinant (Morishima, Y., et al. Supra. 1982).

All E-rosette positive (E-rosette greater than 20%) acute lymphoblastic leukemia (T-ALL) cells have the common characteristics of being DR negative, CALLA negative, 3A1 antigen positive and are positive for 3-3 and 3-40 antigen (Table IIIA). There are four cases listed in Table IIIA as T-ALL which had very low numbers of E-SRBC rosette (1–6%). All four cases had acute lymphoblastic leukemia with thymic involvement.

TABLE III

Study of 3-3 and 3-40 Antigens in Leukemias

A. T Lymphoid Malignancies

| Leu Cells (#) Phenotypes | Peroxidase | E-Ros.* (%) | EA-Ros. (%) | EAC-Ros. (%) | S-Ig | HLA-DR[2] | CALLA[3] | 3A[4] | mAb 3-3 C'-Cytotox. | mAb 3-3 Absorb. Test | mAb 3-40 C'-Cytotox. | mAb 3-40 Absorb. Test |
|---|---|---|---|---|---|---|---|---|---|---|---|---|
| No. 1481 (T—ALL) | — | 92 | 10 | 1 | — | — | — | + | + | + | + | + |
| No. 1141 (T—ALL) | — | 72 | 7 | 24 | — | — | — | + | + | + | + | + |

TABLE III-continued
Study of 3-3 and 3-40 Antigens in Leukemias

| Leu Cells (#) Phenotypes | Peroxi-dase | E-Ros. (%) | EA-Ros. (%) | EAC-Ros. % | S-Ig | HLA-DR[2] | CALLA[3] | 3A1[4] | mAb 3-3 C'-Cytotox. | mAb 3-3 Absorb. Test | mAb 3-40 C'-Cytotox. | mAb 3-40 Absorb. Test |
|---|---|---|---|---|---|---|---|---|---|---|---|---|
| No. 1209 (T—ALL) | − | 72 | 37 | 20 | − | − | − | + | + | + | + | + |
| No. 1266 (T—ALL) | − | 95 | 2 | 3 | − | − | − | + | + | + | + | + |
| No. 838[1] (T—ALL) | − | 6 | 14 | 1 | − | − | − | + | + | + | + | + |
| No. 1267[1] (T—ALL) | − | 1 | 2 | 4 | − | − | − | + | + | + | + | + |
| No. 598[1] (T—ALL) | − | 1 | 1 | 0 | − | − | − | + | + | ND | − | ND |
| No. 1424[1] (T—ALL) | − | 4 | 5 | 4 | − | − | − | − | − | ND | − | ND |
| No. 597 (TL) | − | 68 | 8 | 15 | ND | + | ±[5] | − | − | − | − | − |
| No. 279 (TL) | − | 58 | 5 | 5 | − | − | − | − | ND | ND | + | ND |
| No. 513 (TL) | − | 77 | 1 | 4 | − | + | − | − | − | − | − | − |
| No. 1964 (ATL) | − | 23 | 3 | 2 | − | + | − | − | − | − | − | − |
| No. 1409 (ATL) | − | 44 | 1 | 0 | + | − | − | + | − | − | − | − |

*Ros = Rosette
**Absorb = Absorption

B. Non-T Lymphoid Malignancies

| Leu Cells (#) Phenotypes | Peroxi-dase | E-Ros. (%) | EA-Ros. (%) | EAC-Ros. % | S-Ig | HLA-DR[2] | CALLA[3] | 3A1[4] | mAb 3-3 C'-Cytotox. | mAb 3-3 Absorb. Test | mAb 3-40 C'-Cytotox. | mAb 3-40 Absorb. Test |
|---|---|---|---|---|---|---|---|---|---|---|---|---|
| No. 514 (N—ALL) | − | 2 | 0 | 3 | − | + | + | + | − | − | + | + |
| No. 1277 (N—ALL) | − | 2 | 0 | 12 | − | + | + | − | − | − | + | + |
| No. 542 (N—ALL) | − | 2 | 1 | 3 | − | + | + | − | − | ND | + | ND |
| No. 950 (N—ALL) | − | 0 | 0 | 1 | − | + | + | − | − | ND | − | ND |
| No. 795 (N—ALL) | − | 0 | 2 | 0 | − | + | + | − | − | ND | + | ND |
| No. 1478 (N—ALL) | − | 4 | 6 | 3 | − | + | + | − | − | − | + | + |
| No. 260 (B—ALL) | − | 0 | 1 | 38 | − | + | + | − | − | ND | − | ND |

C. Myeloid Malignancies

| Leu Cells (#) Phenotypes | Per-oxi-dase | N—ASD—C[6] | —N—b-[6] | E-Ros. (%) | EA-Ros. (%) | EAC-Ros. (%) | HLA-DR[2] | CALLA[3] | 3A1[4] | mAb 3-3 C'-Cytotox. | mAb 3-3 Absorb. Test | mAb 3-40 C'-Cytotox. | mAb 3-40 Absorb. Test |
|---|---|---|---|---|---|---|---|---|---|---|---|---|---|
| No. 1307 (AML) | + | ± | − | 1 | 3 | 1 | + | − | + | − | − | − | − |
| No. 1300 (AML) | + | ++ | − | 2 | 0 | 0 | + | − | − | − | − | − | − |
| No. 576 (AML) | + | + | − | 0 | 16 | 0 | + | − | − | − | − | − | − |
| No. 1376 (AML) | + | ± | − | 0 | 1 | 6 | + | − | − | − | − | + | + |
| No. 1283 (AMOL) | + | − | + | 1 | 89 | 10 | − | − | − | − | − | − | − |
| No. 186 (AMOL) | + | ± | + | 0 | 12 | 12 | + | − | − | − | − | − | − |
| No. 2017 (AMOL) | + | ND | ND | 3 | 83 | 18 | ND | ND | ND | − | − | − | − |

Legend to Table III:
ND denotes not done.
[1] Four cases of ALL are included in the listing of T-ALL because they had thymic involvement and/or T cell phenotype (i.e., HLA-DR negative, CALLA negative and 3A1 positive) despite less than 20% E-rosetting.
[2] Detected by monoclonal antibody 6A.
[3] Detected by monoclonal antibody NL-1.
[4] Detected by monoclonal antibody 1-3.
[5] In C'-cytotoxicity test for leukemia cells, more than 90% killing was obtained in all positive cases, while less than 20% killing in all negative cases. Only No. 597 cells showed the intermediate value (i.e., 50%) in spite of repeat testings.
[6] For both esterase stainings, the intensities were graded into 4 classes: i.e., −, ±, +, and ++.
wherein − = no staining
± = weak staining
+ = positive staining
++ = strong positive staining In addition, they did not express the CALLA or the DR antigens and lacked surface immunoglobulins. Three of the four cases express the 3A1 antigen and had either 3-3 and 3-40 antigen (Case 838 and Case 1267) or 3-3 antigen (Case 598). Case 1424 lacked 3A1 antigen and did not express either the 3-3 or 3-40 antigen. This patient, however, had a thymoma. One of the two T-lymphomas (Case 597) had DR positive and weakly CALLA positive leukemia cells and is therefore unusual from the previously reported phenotype of T-lymphoma (Halper, J. P., et al. Blood 55: 373, 1980). This case was also negative for 3-3 and 3-40 antigen.

Two of three (ATL (Case 573 and Case 1964) had the characteristic phenotype of ATL as previously reported (Hattori, T., et al. Blood 58: 645, 1981; Catovsky, D., et al. Lancet 1: 639, 1981), while one case (Case 1409) is atypical because the leukemia cells were surface Ig positive, DR positive, and 3A1 antigen positive. None of the ATL expressed the 3-3 and 3-40 antigen.

Non-T-lymphoid leukemia demonstrated the differences between the 3-3 and the 3-40 antigens. E-, EA- and EAC-negative ALL (N-ALL) cells were also lacking surface immunoglobulin, but were DR positive, and CALLA positive. One case (Case 514) was unusual in that is was positive for the 3A1 antigen. The 3-3 antigen was not found on any of the six N-ALL cells, while 3-40 antigen was present on five of the six N-ALL cells. One B-ALL (Case 260) was surface Ig negative, DR positive, CALLA positive, 3A1 negative and negative for both 3-3 and 3-40 antigen (Table IIIB).

The acute myelocytic leukemia cells (AML) were generally DR positive, CALLA negative, and 3A1 antigen negative except No. 1307, which expressed 3A1 antigen. One of the AML cases (Case 1379) was, however, positive for 3-40 antigen both in C'-cytotoxicity testing and by absorption. Cell No. 1307 was positive for 3-40 antigen only by absorption. All monocytic leukemia (AMOL) cases (Case 1283, Case 1861, and Case 2017) had high ratio of the EA-rosetting and were negative for CALLA, 3A1, 3-3 and 3-40 antigens.

The results of the serological analysis of these leukemias using mAb 3-3, mAb 3-40 and mAb 1-3 are summarized in Table IV below.

Studies were performed in order to determine if mAb 3-3 and mAb 3-40 were reactive with the same epitope on the same molecule, even though the two antibodies had somewhat different tissue distributions. This was studied by the "double absorption" test as described above. mAb 3-3 can be completely removed by absorption with MOLT 4 from hybridoma culture supernatant diluted 1:150. Cell lines which did not express the 3-3 antigen were unable to remove significant amounts of antibodies. When MOLT 4 cells were saturated after incubation with high titered mAb 3-40, these coated cells were still able to remove mAb 3-3 to the same extent as uncoated MOLT 4, while the MOLT 4 cells coated with mAb 3-3 prior to absorption with mAb 3-3 were unable to remove additional 3-3 antigen. Reciprocal absorption experiments were performed for mAb 3-40. While the MOLT 4 cells saturated previously with high tiltered mAb 3-3 were still able to remove mAb 3-40 as well as uncoated MOLT 4 cells, mAb 3-40 could not be removed by MOLT 4 cells coated with mAb 3-40 prior to absorption. These studies indicate that the two antibodies are not reactive with the same epitope of the same molecule or determinants which are in close proximity on the cell surface.

EXAMPLE 3

Expression of 3-3 and 3-40 antigens in tissue sections

Table V below summarizes the results of the histological analysis of the 3-40 antigen. Among normal tissues, mAb 3-40 was reactive with the epithelium and a few lymphoid cells in the thymus, and occasional cells in normal lymph nodes. Positive cells were also found in the sebaceous glands of the skin, the stroma of the uterus, fetal testis tubules and Langerhans islet cells is the pancreas.

TABLE IV

| Differential Diagnosis of Leukemia by mAbs 3-3 and 3-40 | | E-Rosette | 3-3 | 3-40 | 1-3 |
|---|---|---|---|---|---|
| T-cell leukemia | | | | | |
| Early Stage | T-ALL | +/− | + | + | + |
| Late Stage | CTCL | + | − | − | − |
| | ATL | + | − | − | − |
| | T-CLL | + | − | − | − |
| Other Leukemia | | − | − | +/−* | − |

*Some non-T, non-B ALL and a few AML cells are also positive for 3-40 antigen.

In malignant tissues, mAb 3-40 reacted with tumor cells in some melanoma, breast cancer, ovarian cancer and colon cancer specimens. The 3-3 antigen was not found on any tissues tested so far.

EXAMPLE 4

Biochemical analysis of 3-3 and 3-40 antigen

A biochemical analysis was performed using mAb 3-3 and mAb 3-40 to immunoprecipitate these antigens from lysates of $^{125}$I labeled MOLT 4 cells. Their molecular weights were analyzed by SDS polyacrylamide gel electrophoresis under reducing conditions and compared with the human thymus leukemia-like antigens immunoprecipitated from the same lysates using M241 [Knowles, Supra (1982)] and NA1/34 (McMichael, Supra). Both the 3-3 and 3-40 antigens labeled and immunoprecipitated in this way showed similar mobilities on 12.5% gels with somewhat heterogeneous patters in the molecular weight range of 35–40,000 daltons. The mobility of the 3-40 antigen was somewhat faster than the mobility of the 3-3 antigen on 15% gels.

In comparing the mobility of these antigens with the mobility of the HLA-A,B,C antigens precipitated from the same lysate by W6/32 and the mixture of $B_2$(Beta sub-two)-microglobulin ($B_2$-m) associated molecules precipitated by BBM.1, which include the HLA-A,B,C antigens, the M241 precipitable molecules and a portion of the NA1/34 precipitable molecules (Knowles, R. W., et al., Springer-Verlag, Berlin (in press), 1983), there is some overlap between the mobility of the 3-3 molecules and the mobilities of the $B_2$-m associated heavy chains. No distinct $B_2$-m sized subunits were visible in the 3-3 or 3-40 immunoprecipitates. Sequential immunoprecipitation will be necessary to determine whether weakly labeled $B_2$-m subunits are associated with these heavy chains, as they were found associated with the M241 heavy chains (Knowles, Supra 1982).

TABLE V

| Summary of Histological Testing mAb 3-40 | |
|---|---|
| Normal tissues examined | |
| thymus | epithelial cells; Hassal's corpuscles; a few lymphoid cells |
| pancreas | islets of Langerhans' cells |
| lymph node | a few lymphoid cells diffusely stained |
| uterus | stroma |
| ovary | negative |
| testis | negative |
| fetal testis | tubule |
| skin | sebaceous gland |
| kidney | negative |
| brain | negative |
| lung | negative |
| colon | negative |
| esophagus | negative |

TABLE V-continued

| Summary of Histological Testing mAb 3-40 | |
| --- | --- |
| liver | negative |
| thyroid | negative |
| skeletal muscle | negative |
| Malignant tissues examined | |
| melanoma | 8/14 |
| lung cancer | 0/2 |
| breast cancer | 1/2 |
| renal cancer | 0/4 |
| ovarian cancer | 5/6 |
| colon cancer | 1/4 |

*No. of positive cases/No. of total cases

EXAMPLES 5

Heat denaturation

One of the physicochemical characteristics of the 3-3 and 3-40 antigens was examined by testing their sensitivity to heat denaturation. MOLT 4 cells were heated to 100° C. for 5 min and compared with cells at room temperature for their ability to absorb mAb 3-3 or mAb 3-40. While this heat treatment destroyed the ability of MOLT-4 cells to absorb mAb 3-3, these cells remained fully capable of absorbing mAb 3-40, indicating that the 3-40 antigen is extremely resistant to heat denaturation.

Thus, murine monoclonal antibodies have been produced which detect two new leukemia associated antigens predominantly expressed on T-ALL. The antigens are generally expressed on T-ALL cell lines and leukemic cells which also express the normal T lymphocyte antigen 3A1 (Haynes, Supra (1979). The antibodies appeared to detect two different antigens, since some cells are positive for 3-3 antigen, while negative for 3-40 antigen (i.e., T-ALL line HOGAN and one fresh T-ALL), and 3-40 antigen is present on some cells where 3-3 antigen is absent (i.e., T-ALL line HSB-2 and one T-cell lymphoma). The most important difference in the hemitopoietic tissue distribution of 3-3 and 3-40 antigens is that the 3-40 antigen is also present on several N-ALL cells and on two AML.

Recently, a murine monoclonal antibody (CALLA-2) was described by Deng et al. Supra, which had a similar tissue distribution on T cell lines and fresh T-ALL cells. Other monoclonal antibodies have been produced following immunization with purified human thymus leukemia antigens (Seon, B. K., et al. J. Immunol. 127: 2580, 1981) which have specifications which are similar to CALLA-2 on a limited panel of T cell lines (Negoro, S., et al. Cancer Res. 42: 4259, 1982). In contrast, the CALLA antigen detected by mAb J-5 is broadly distributed on ALL cells and only present on a few T-ALL cell lines (Ritz, Supra), and is therefore clearly different from the antigens detected by mAb 3-3 and mAb 3-40. Ueda et al, Supra have recently reported mAb NL-22 which identifies an antigen which is identical to J-5. Tis NL-22 antigen is not expressed on any T cell lines or fresh T-ALL cells and therefore it is distinct from 3-3 and 3-40 antigens. The 3-3 and 3-40 antigens are also different from the P 9 antigen of the human retrovirus (HTLV) isolated from cutaneous T-cell lymphoma derived cell lines (Poiesz, Supra) and from the antigen (ATLA) associated with the human retrovirus isolated from adult T-cell leukemia derived cell line (Miyoshi, I. et al. Nature 294: 770, 1981). Neither antibody reacted with the two cutaneous T-cell lymphoma cell lines HUT-102 (producer of HTLV) and HUT-78 (non-producer of HTLV). Moreover, three Sezary cells and three adult T leukemia (ATL) cells failed to react with the two antibodies. The 3A1 antigen was found to be present on 80% of normal T lymphocytes. This antigen is expressed on T-ALL, while absent from cutaneous T cell leukemia (CTCL) and ATL, as previously reported (Haynes, Supra, 1979 and 1981, Morishima, Supra). Since the reactivity of mAb 3-3 and mAb 3-40 with thymocytes was different from the reactivity of NA1/34 (McMichael, Supra) and M241 (Knowles, Supra 1982), 3-3 and 3-40 antigens are clearly different from the human TL-like antigens. Since they do not react with mitogen or alloantigen activated cells or long-term cultured T lymphocyte clones, they are also different from the Tac antibody which detects the interleukin-2 receptor (Uchiyama, T. et al. J. Immnol. 126: 1393, 1981).

A pattern of several major groups of T lymphoblastic leukemia emerges from the study of cell surface phenotyping by monoclonal antibodies (Table IV). We describe in this report four cases of acute lymphoblastic leukemia, with very low number of SRBC-rosette forming cells (1–6%). All four leukemia cells also lack the expression of DR, CALLA and surface Ig. Three of these leukemias expressed the 3A1 antigens and the 3-3 antigen, while two of these were positive for 3-40 antigen as well. Therefore, T-ALL consists of at least two major groups. One has a high number of SRBC rosetting cells and is positive for 3A1, 3-3 and 3-40 antigens. The second group has a very low number of SRBC rosetting cells, but is still positive for 3A1, 3-3, and 3-40 antigens. The cutaneous T cell leukemias (T-CLL) which express the retrovirus antigen p19 lack the 3A1 antigen and these cells do not express 3-3 or 3-40 anitigens. Adult T cell leukemia (ATL) cells do not express 3-3 or 3-40 antigen and are negative for 3A1 antigen. It has been described that the late stage T lymphoid malignancy exemplified by CTCL, ATL, and T-CLL can be further classified according to the T-cell phenotype and function; i.e., into Leu-2 (OKT-8) positive suppressor cells and into Leu-3 (OKT-4) positive helper cells (Reinherz, Supra; Haynes, Supra (1981), Hattori, T. et al. Blood 58: 645, 1981; Boumsell, L. et al. Blood 57: 526, 1981; Kung, P. C., et al. Blood 57: 261, 1981; Gramatzki, M. et al. Blood 59: 702, 1982). There are, however, exceptions to such classifications. One of the ATL studied in this report (Case 1409) has an atypical phenotype of great interest; i.e., positive for SRBC rosettes, and surface Ig and 3A1 antigen, but negative for DR, CALLA, 3-3 and 3-40 antigens. It has been suggested that neoplastic lymphoid cells can form rosettes through their surface Ig rather than through classical T cell sheep erythrocyte receptors (Borelle, S. L. J. Immunol. 114: 187, 1975). Boumsell et al. Supra have, however, reported one case of T-CLL associated with monoclonal IgG lambda in the patient's serum, where the cells were phenotypically inducer/helper cells. It cannot be determined if the expression of both T- and B-cell markers on the leukemia cells in Case No. 1409 represents a monoclonal expansion of a malignant cell with this abnormal expression due to malignant transformation, or whether one set of markers has been acquired. The expression of the pan T-lymphocyte antigen Leu 1 (OKT 1) by B-CLL could reflect a similar phenomenon (Wang, C. Y. et al. J. Exp. Med. 151: 539, 1980; Martin, P. J., et al. Immunogenetics 11: 429: 1980).

The histopathological examination showed that 3-40 antigen exists on several normal tissues, including epithelial cells and a few lymphoid cells in the thymus and islets of Langerhans cells in the pancreas, and on several malignant tissues including melanomas, although serological studies using C'-cytotoxicity, absorption and indirect immunofluorescence assays failed to demonstrate any reactivity of mAb 3-40 against normal hematopoietic cells in suspension. Recently, Eisenbarth et al (Eisenbarth, G. S., et al. Proc. Nat'l. Acad. Sci. USA 76: 49 3, 1979) described the mAb A2B5 reacting with a complex neural G2 ganglioside expressed on the cell surface of neurons, neural crest derived cells, and peptide-secreting endocrine cells. This antibody also reacts with thymic epithelial cells (Haynes, B. F., et al. J. Clin. Invest. 71: 9, 1983). The 3-40 antigen is also expressed on thymic epithelial cells. The 3-40 antigen could, however, still be a normal lymphoid differentiation antigen which is only transiently expressed on thymocytes and not detected by our serological techniques. Alternatively it is possible that the 3-40 antigen is not expressed on normal hematopoietic cells but is only expressed on T-ALL cells following malignant transformation. This would support the concept that the thymic epithelium plays a role in leukemogenesis (Zielinski, C. C. et al J. Immunol. 129: 882, 1982).

Biochemical studies of the 3-3 and 3-40 antigens have demonstrated that $^{125}I$ labeled molecules can be immunoprecipitated from lysates of surface labeled MOLT 4 cells. The 3-3 and 3-40 antigens had mobilities on SDS polyacrylamide gels which correspond to proteins with apparent molecular weights of 35-40,000 daltons on 12.5% gels. The 3-40 antigen shifts however, to a faster mobility ion 15% gels relative to the 3-3 antigen.

These antibodies appear to recognize distinct antigens based on the differences in their tissue distributions and the difference in their mobility of 15% gels. The "double absorption" technique demonstrated that MOLT 4 cells saturated with either antibody remain fully capable of absorbing the other antibody. Another difference between these antigenic determinants is their heat stability.

Although there is some overlap between the mobility on 15% gels of the 3-3 molecule and the mixture of $B_2$-m associated heavy chains immunoprecipitated with BBM.1, there is no evidence for a $B_2$-m like subunit associated with either the 3-3 or 3-40 antigens. Further analysis using sequential immunoprecipitation is in progress to determine whether any weakly labeled $B_2$-m subunits are bound to these antigens.

Preliminary in vitro studies using mAb 3-3 and mAb 3-40 have demonstrated that treatment of bone marrow cells with these antibodies in the presence of complement does not produce significant inhibition of Colony Forming Units in Culture (CFU-C) growth. These antibodies may therefore be applicable for the in vitro purging of leukemic cells prior to autologous bone marrow transplantation of patients whose leukemic cells express these antigens similar to the studies performed with mAb J5 (anti-CALLA) (Ritz, J. et al. Blood 58: 141, 1981; Ritz, J. et al. Lancet. II: 60, 1982). The mAb 3-40 recognition of pancreatic langerhans cells has potential in diabetics diagnosis and treatment. Early diagnosis for diabetes involves detection of diabetes auto-antibody-(ies) by isolated cellular antigenic determinants such as those determinant components which react with any auto-antibody of diabetes. Cellular antigenic components which serve as antigen for mAb 3-40 would be one such detection device. mAb 3-40 is another detection system which reacts with human body tissue, fluid or exudate samples to detect diabetes.

Monoclonal antibodies 3-3 and 3-40 are on deposit and available at Sloan-Kettering Institute, Human Immunogenetics Section, Department of Clinical Immunology, 1275 York Avenue, New York, N.Y. 10021.

Monoclonal Hybridoma cell lines CL 3-3 and CL 3-40 producing respectively antibodies 3-3 and 3-40 have been deposited with the American Type Culture Collection (ATCC), 12301 Parklawn Drive, Rockville, Md. 20852 on Sept. 29, 1983 and have been given ATCC accession numbers of HB8369 for hybridoma cell line CL 3-3 producing mAb 3-3, and HB8368 for hybridoma cell line CL 3-40 producing mAb 3-40.

What is claimed is:

1. Monoclonal antibody 3-3 (HB8369) and 3-40 (HB8368) not capable of immunological reaction with normal, human peripheral T or B blood cell antigens, normal human thymocyte antigens or normal, human bone marrow precursor cell antigens but capable of immunological reaction with separate and distinct T-ALL leukemia antigens (T-ALL) having molecular weights of approximately 35-40,000 KD and wherein said monoclonal antibodies are capable of distinguishing T-ALL leukemia from cutaneous T-cell lymphoma (CTCL), adult T cell leukemia (ATL) and T-cell chronic lymphocytic leukemia (T-CLL) and further capable of subsetting T-ALL leukemia into E-Rosette positive and E-Rosette negative cells.

2. Monoclonal antibody of claim 1 wherein monoclonal antibody 3-40 is further capable of immunological reaction with antigen from the group of cells comprising non-T, non-B ALL cells, AML cells, epithelial cells, langerhans cells, and malignant tissues from the group of melanoma, breast, ovarian and colon cancers.

3. Antibody producing hybridoma cell line 3-3 (HB8369) and 3-40 (HB8368) characterized by the production of monoclonal antibody 3-3 and 3-40 wherein 3-3 and 3-40 are not capable of immunological reaction with normal, human peripheral T or B blood cell antigens, normal human thymocyte antigens or normal human bone marrow precursor cells but are capable of immunological reaction with separate and distinct T-ALL leukemia antigens having molecular weights of approximately 35-40,000 KD and wherein said monoclonal antibodies are capable of distinguishing T-ALL leukemia from cutaneous T-cell lymphoma (CTCL), adult T cell leukemia (ATL) and T-cell chronic lymphocytic leukemia (T-CLL) and further capable of subsetting T-ALL leukemia into E-Rosette positive and E-Rosette negative cells.

4. Cell line of claim 3 wherein the hybridoma is produced from the fusion of MOLT-4 immunogen treated splenocytes and NS/1 myeloma cells.

5. Method for differential diagnosis of T-ALL leukemia from cutaneous T-cell lymphoma (CTCL), adult T-cell leukemia (ATL) and T-cell chronic lymphocytic leukemia (T-CLL) which comprises contacting a suspected human hematopoietic T-ALL leukemic specimen with monoclonal antibody of claim 1, and detecting any immunological reaction.

6. Method for diagnosing T-ALL leukemia which comprises contacting a suspected human hematopoietic T-ALL leukemic specimen with monoclonal antibody of claim 1 and detecting the extent of immunological reaction.

7. Method of subsetting and detecting T-ALL leukemia cells which comprises contacting T-ALL leukemic cells which react immunologically with mAbs 3-3 (HB8369) and 3-40 (HB8368) with sheep red blood cells and observing sheep red blood rosette cells from the group consisting of E-Rosette negative (1-6% sheep red blood rosette cells) and E-Rosette positive (greater than 20% sheep red blood rosette cells).

* * * * *